United States Patent [19]

Samiy et al.

[11] Patent Number: 5,653,751
[45] Date of Patent: Aug. 5, 1997

[54] SYSTEMS AND METHODS FOR PROJECTING AN IMAGE ONTO A RETINA

[76] Inventors: Nassrollah Samiy, 34 Hancock St., #3B, Boston, Mass. 02114; John D. T. Gerber, 49 E. 92nd St., #4B, New York, N.Y. 10128

[21] Appl. No.: 350,568

[22] Filed: Dec. 7, 1994

[51] Int. Cl.⁶ .................................................. A61F 2/14
[52] U.S. Cl. ............................ 623/4; 623/5; 128/899
[58] Field of Search ........................... 128/899; 623/4–6

[56] References Cited

U.S. PATENT DOCUMENTS

| 4,213,678 | 7/1980 | Pomerantzeff et al. |
|---|---|---|
| 4,579,430 | 4/1986 | Bille. |
| 5,076,275 | 12/1991 | Bechor et al. ............... 128/653.2 |

OTHER PUBLICATIONS

Webb et al., "Flying Spot TV Ophthalmoscope", Applied Optics, vol. 19, No. 17, pp. 2991–2997 (Sep. 1980).
Bille et al, "Laser Scanning Ophthalmoscope with Active Focus Control", The Institute of Electrical and Electronics Engineers, Part 1, Proc. 6, 1226 (1982 IEEE).
Minkowski et al., "New Methods for Predicting Visual Acuity After Cateract Surgery", Annals of Opthalmology, vol. 16, No. 6, pp. 512–516 (Jun. 1984).
Guyton, "Instruments for Measuring Retinal Visual Acuity Behind Cataracts—1982", Opthalmology, Instrument and Book Supplement pp. 34–39 (Aug. 1982).
Minkowski et al. "Potential Acuity Meter Using a Minute Aerial Pinhole Aperture", Opthalmology, vol. 90, No. 11, pp. 1360–1368 (Nov. 1983).

*Primary Examiner*—Ruth S. Smith
*Attorney, Agent, or Firm*—Lahive & Cockfield, LLP

[57] ABSTRACT

Apparatus and methods are described that project images onto the retina of an eye. The apparatus can include an image memory element for storing an image signal representative of a visual image, a projection element in electrical circuit with the image memory element for generating an optical image signal of the type suitable for detection by a retina and being representative of the visual image, and a focus element that is adapted for implantation into the eye at a position in the eye which is posterior to the cornea and anterior to the retina and that is optically coupled to the projection element for focusing the optical image onto the retina. The projection element can include a display device that is dimensionally adapted for disposition within the eye at a position posterior to the cornea. The display device can be a liquid crystal display element that has an illuminator element optically coupled to the display device or alternatively can include a laser diode element that optically couples to a scanning mirror that projects light through a damaged cornea.

23 Claims, 6 Drawing Sheets

SYSTEMS AND METHODS FOR PROJECTING AN IMAGE ONTO A RETINA

FIELD OF THE INVENTION

The present invention relates generally to medical devices and processes that alleviate vision impairment. More particularly, the invention relates to medical devices and processes that project images onto the retina of an eye. Most particularly, the invention relates to electronic keratoprostheses and processes for using electronic prostheses that can be surgically implanted into an eye having a damaged cornea, retinal macular degeneration, optic neuropathy or other such conditions that substantially degrade or obstruct the projection of images to the retina.

BACKGROUND OF THE INVENTION

Every year corneal opacity blinds or visually impairs thousands of people. The causes of corneal opacity are quite diverse, and consequently the members of the afflicted population suffer a wide range of conditions. Importantly, researchers have identified among the afflicted population, individual patients with corneal opacity that is blinding an otherwise healthy eye. Therefore, a major goal of ophthalmology is to find a treatment that alleviates corneal opacity to restore to these members of the afflicted population their ability to see.

A healthy cornea is an almost perfectly transparent layer of tissue that projects forward from the anterior portion of the eye. The transparent cornea acts like a window that lets light and images enter into the eye, pass through the crystalline lens and project onto the retina.

The retina is positioned at the posterior portion of the eye and at a distance of about one inch from the cornea. The retina is a delicate nervous membrane upon the surface of which the images of external objects are received. The retina is an exceedingly complex structure having many layers of cells and nerve fibers which connect to the optic nerve. It is understood that the retina detects the light and the images that enter the eye through the cornea, and that the images that a person sees are caused by the projected images that stimulate the photoreceptors in the retina.

Although the cornea and the retina are distinct parts of the eye, both parts must function properly for the eye to correctly perceive images. Damage to either the retina or the cornea can impair a person's vision.

Corneal opacity impairs vision by preventing light from reaching the retina. The condition of corneal opacity can arise from a wealth of different situations including trachoma, a chronic and contagious form of conjunctivitis, which is the second most common cause of blindness in the world. Commonly, scarring from abrasive physical contact, chemical exposure, and burning can destroy or damage the corneal tissue and can create scar tissue that turns the cornea opaque or cloudy. In other cases, severe lacrimal fluid deficiency, or dry eye syndrome, can compromise the corneal tissue with scarring. Additionally, infections or severe allergic reactions to various drugs can cause scarring of the lid under surface which, in turn, results in repetitive microtrauma to the corneal surface. This is a persistent condition that, over the long term, results in corneal scarring and obstructed vision.

Just as the causes of corneal opacity can vary widely, so too can the extent of the scarring and the degeneration. However, regardless of the cause or the extent, the resultant corneal damage can substantially impair the patient's vision.

In cases of severe damage the corneal tissue can be permanently and totally impaired, thereby causing blindness in the patient due to insufficient light passing through the cornea. Even in the case of sparse scarring or clouding, the degenerated corneal epithelium can substantially decrease visual acuity.

However, although the patient's vision is lost or substantially impaired due to the damage to the cornea, the patient may still retain a healthy retina and therefore have a significant potential visual acuity. For example, researchers have identified patients who have substantially opaque corneas but are still able to detect light when the light is projected with sufficient intensity against the surface of the damaged cornea. This indicates that the patient has a functioning retina and possibly a significant potential visual acuity. More recently, researchers have identified patients that can "read" a Snellen chart if the chart is projected into the eye by light of sufficient intensity. These tests have been performed to identify the candidate patients whom are likely to benefit from a surgical procedure that could correct the vision impairment caused by the medial opacity, such as a cataract.

Conventional surgical techniques exist for treating the corneal opacity of some patients. Typically, the candidate patient has suffered substantial corneal damage, but the eye in general is well shaped and the retina appears healthy. These techniques, such as cadaveric corneal graft involve surgically removing the damaged cornea and attaching an optical prosthesis, an artificial cornea, to the eye. The optical prosthesis is a transparent membrane that functions just as a healthy cornea, to allow light into the eye.

Although this technique offers help to some patients, it cannot always be practiced on patients who have suffered severe damage to the anterior segment of the eye. Furthermore, the optical prosthesis is extremely prone to extrusion, as it is attached to the outer corneal layer, and is easily sloughed off the eye by occurrences of rejection. Another problem with the optical prosthesis is that tissue can grow over the attached prosthesis, and prevent light from entering the eye. Furthermore, tissue can grow under the prosthesis and block light from the eye, as well as tear the prosthesis from the eye. These and other problems have hampered the use of optical prostheses to bring relief to the afflicted population.

Accordingly, it is an object of the present invention to provide improved systems and methods for alleviating vision impairment caused by corneal opacity.

It is a further object of the present invention to provide medical apparatus and procedures for alleviating corneal opacity that are less affected by the growth of biological tissue.

It is still a further object of the present invention to provide medical apparatus and procedures that are less dependent on the optical properties of a prosthetic device.

It is yet another object of the present invention to provide medical apparatus and procedures that are less affected by the affects of prosthesis extrusion.

It is still another object of the present invention to provide medical apparatus and procedures for alleviating vision impairment caused by corneal opacity in patients having substantial damage to the cornea, the interior portions of the eye, the retina, the optic nerve or other natural optic structure.

These and other general and specific objects of the present invention will become apparent from or appear in the following description of the invention.

SUMMARY OF THE INVENTION

The present invention provides electronic keratoprostheses that project images onto the retina of an eye. In one embodiment, the electronic keratoprostheses employ display panel technology to provide a surgically implantable image projection system that can, in part, fit behind the damaged cornea and generate images that are detectable by a healthy retina or a healthy portion of a retina. The electronic prosthesis generally includes an image source, a projection element for projecting images onto the retina and a focusing element. Therefore, in one aspect of the present invention, an active keratoprosthesis is realized that provides images and projects images onto the retina.

In one aspect of the invention, keratoprostheses are provided that include an image memory element for storing an image signal representative of a visual image, a projection element in electrical circuit with the image memory element, for generating an optical image signal of the type suitable for detection by a retina and being representative of the visual image, and a focus element that is adapted for implantation into the eye at a position in the eye which is posterior to the cornea and anterior to the retina and that is optically coupled to the projection element for focusing the optical image onto the retina.

In one embodiment of the invention, the projection element includes a display device that is dimensionally adapted for disposition within the eye at a position posterior to the cornea. The display device can be a liquid crystal display element that has an illuminator element optically coupled thereto. In certain embodiments of the invention, the projection element also includes a beam splitter element that optically couples the illuminator element to the display element and that optically couples the display device to the focus element. In an alternative embodiment, the projection element includes a laser diode element that optically couples to a scanning mirror. The scanning mirror can be a mirror assembly that couples to a control element and in one embodiment, the mirror assembly includes a polygonal mirror that couples to a motor element that rotates the polygonal mirror relative to a longitudinal axis extending through the mirror. In a further embodiment, the projection element includes two polygonal scanning mirrors including a horizontal scanning mirror element that scans a beam of radiation, preferably generated by a laser diode element, across the retina relative to a horizontal axis and can include a vertical scanning mirror element that scans the beam of radiation across the retina relative to a vertical axis. Alternatively, the projection element employs acousto-optic crystals that couple to the control element, to scan the beam of radiation across the retina.

A visual image, as the term is used herein, can encompass optically communicated information including optical reproductions of an object or optically represented information such as by text, symbols or color.

In another embodiment of the present invention, the keratoprosthesis includes an image collection element connected in electrical circuit with an image memory element, for generating and storing an image signal. In one embodiment the image collection element includes a digital camera element having a charge coupled device. In other embodiments of the present invention, the image collection element includes a data processing element that has an image signal generator for generating digital data signals that can represent a visual image. The memory element can include an electrical circuit data memory of the type that is suitable for storing electrical digital data signals.

In another aspect of the present invention, the focus element includes a lens element that has a focal length adapted for projecting the optical images projected by the projection element onto a select portion of the retina. The lens element can be formed from a biocompatible material, preferably polymethylmethacrylate (PMMA).

In a further aspect of the invention, the focusing element includes an adjustable lens that is adapted for selectively optically coupling with a crystalline lens of the eye. The adjustable lens can be arranged for achieving a selected focal length and can further optionally include an optical steering element that communicates a projected image to a select portion of the retina.

In another embodiment of the invention, the keratoprosthesis is in part dimensionally adapted for being surgically implanted within an eye at a location posterior to the impaired cornea. In this embodiment the prosthesis includes a projection element and focusing element that are dimensionally adapted for implantation into the eye at a position posterior to the cornea and anterior to the retina, and that couple, via a data coupling element, in electrical circuit with the image memory element. The data coupling element can provide radio, or infra-red transmission or can provide a data cable that exits the eye through a surgical canal.

In yet another embodiment of the present invention, the apparatus provides a projection element that can be positioned exterior to the eye. The projection element can include a laser diode that generates an optical image signal of sufficient intensity to pass through the substantially opaque cornea. The focusing element can be a lens element formed from a biocompatible material and surgically implanted posterior to the cornea. The lens element focuses the projected optical image onto the retina.

In another aspect of the present invention, methods are provided for projecting an image onto a retina. Generally, the methods include steps for storing an image signal representative of a visual image, projecting the stored image signal as an optical image signal of the type suitable for detection by a retina, and providing a focusing element that is adapted for implantation into the eye at a position posterior to the cornea and anterior to the retina and that is optically coupled to the projection element for focusing the projected optical image onto the retina. In another aspect of these embodiments, the step of projecting an optical image includes the steps of providing a projection element that includes a display device that is dimensionally adapted for disposition within the eye at a position posterior to the cornea. The step of providing a display device can include the particular step of providing a liquid crystal display device that has an illuminator element that optically couples to the display device and the step of providing a projection element can further include the step of providing a beam splitter element that optically couples the illuminator element to the display device and that optically couples the display device to the focus element.

In another aspect of these embodiments, the step of projecting an optical image onto a retina includes the step of providing a laser diode element that is optically coupled to a scanning mirror. This embodiment can also include the step of rotating a polygonal scanning mirror to scan the beam generated by the laser diode across the retina relative to a first axis and a step for providing a second scanning mirror that scans the beam generated by the laser diode across a second axis extending transverse relative to a vertical axis. Alternatively, this embodiment can include the step of providing acoustic optical crystals that optically couple to the projected image and scan the image across the retina.

In another aspect of these embodiments, a process for projecting an image onto a retina includes the steps of providing an image collection element that generates the image signal stored in the image memory. The image collection element can include a digital camera element that has a charge coupled device. The image collection element may include a data processor element that generates an image signal. The step of focusing an image onto a retina can include the step of providing a lens element that has a focal length adapted for projecting the optical image signal onto a select portion of the retina. In a further aspect of the present invention, the lens element is adjusted to project images to a select portion of the retina.

A fuller understanding of the nature and the objects of the invention can be understood with reference to the following description of exemplary embodiments of the present invention.

A BRIEF DESCRIPTION OF THE DRAWINGS

DETAILED DESCRIPTION OF THE ILLUSTRATED EMBODIMENTS

Figure 1:
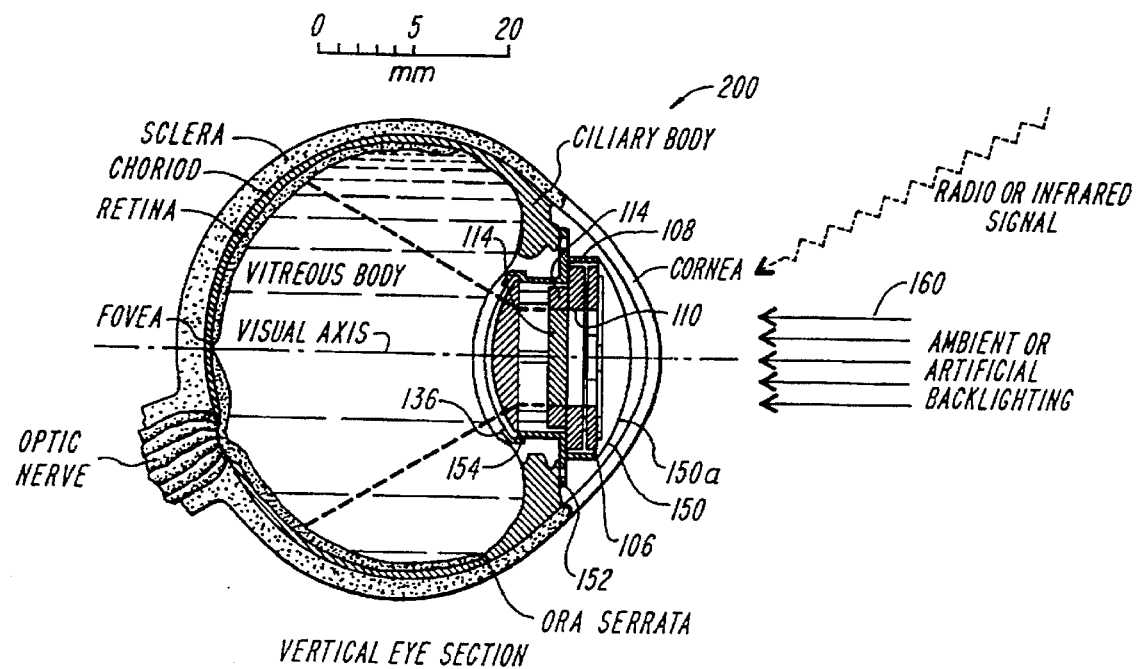
FIGS. 1–4 illustrate a first embodiment of the present invention for projecting images onto the retina of an eye.

FIGS. 1–4 illustrate a first embodiment of the present invention for projecting images onto the retina of an eye. FIG. 1 illustrates a first system 200 that comprises an electronic keratoprosthesis that can in part be surgically mounted behind the cornea of the eye. The system 200 includes a clear cover element 150, a battery pack assembly 106, a transmitter receiver element 108, a screen driver control circuit element 110, a display panel 114, an adjustable imaging lens 136, a suture ring housing 152, and a lens retainer ring 154.

As illustrated in FIG. 1, the apparatus 200 is an implantable electronic keratoprosthesis that fits posterior the cornea and surgically attaches within the vitreous cavity of the eye. The depicted display panel 114 sits between a source of ambient or artificial light 160 and an imaging lens focusing element 136. The display panel 114 modulates the incoming light 160 to generate optical image signals that can be detected by the retina of the eye. The imaging lens focusing element 136 focuses the optical image signals onto the retina. The transceiver element 108 is in electrical circuit with the display panel and includes a display driver circuit element that operates the display panel 114 to modulate the incoming light 160. The illustrated transceiver element 108 also includes a receiver element that receives information signals that can be used to control the image signal generated by the display panel 114.

The illustrated cover element 150 is a transparent cover element formed of a biocompatible material, such as PMMA, that fluidicly isolates the internal elements of the device 200 from the biological tissue, including the fluids, of the eye. The cover element 150 illustrated in FIG. 1 has a concave exterior wall 150A that, in the illustrated embodiment, follows the form of the cornea and can provide a concave support wall about which the cornea can form. As such, the illustrated cover element 150 provides a support wall that stabilizes the shape of the cornea.

Figure 2:
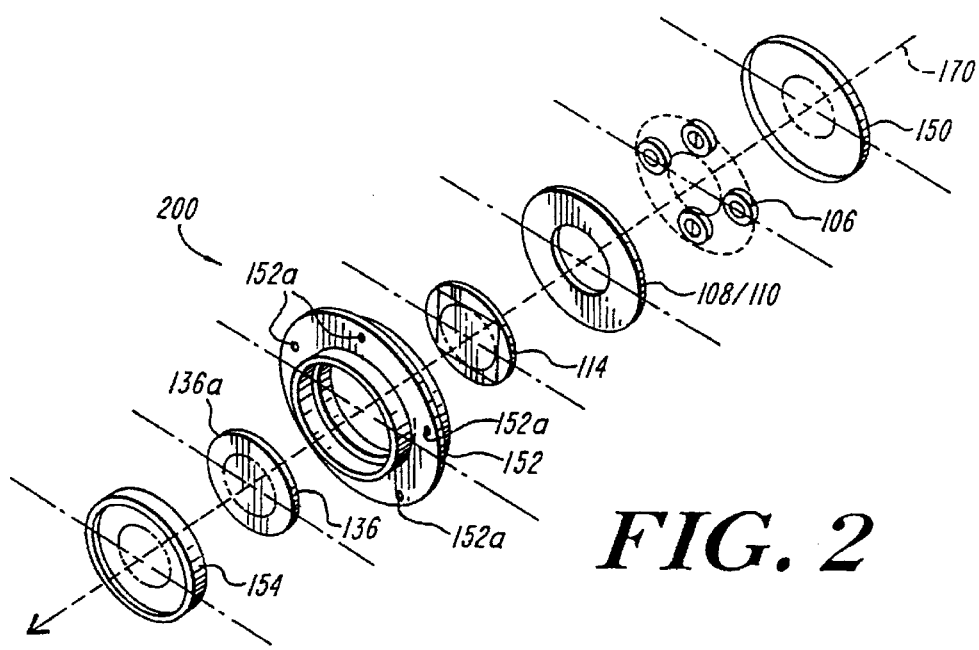

Positioned posterior to the cover element 150 is the battery pack assembly 106. In the illustrated embodiment, as shown in the exploded view, the battery pack 106 comprises four battery elements of the type commonly used for providing a portable battery supply. As illustrated in FIG. 2, the battery pack assembly 106 is arranged about a central aperture though which light can pass. In another embodiment of the invention, the battery pack may be supplemented by electric cells.

The battery pack 106 engages against the transmitter receiver element 108. The transmitter receiver element 108 is an electrical circuit card assembly of conventional design that can receive radio, infra-red, or other electromagnetic signals and process the signal to demodulate information carried therein. The transmitter receiver element can also include ,a display driver circuit element for operating the display panel 114. The construction of the receiver element 108 follows from well known principles in the art of electrical engineering, and the design thereof is considered well within the scope of any one of ordinary skill in the art of electrical engineering. The transmitter receiver 108 contains an optional transmitter element for broadcasting status information, such as battery power, to a receiver element of conventional design. The illustrated transmitter receiver element 108 has a central aperture extending therethrough to allow light to pass through the transmitter receiver element 108 and optically couple with the display element 114.

The display element 114 illustrated in FIG. 1 is a passive display element, preferably for generating high resolution images, and is positioned into optical engagement with the light 160 that is incident on the cornea of the eye 200. The passive matrix display element 114, as will be described in greater detail hereinafter, is of the type commonly used for selectively modulating a light source to provide optical images that are detectable to the human eye and the retina. As illustrated in FIG. 1, the battery pack assembly 106, transmitter receiver element 108, and display element 114 are dimensionally adapted for fitting within the suture ring housing element 152 which has a nipple extending therefrom that is dimensionally adapted for receiving the cover element 150 into frictional engagement for sealing the elements 106, 108 and 114 therein.

The suture ring housing element 152 is a ring that has a central aperture and is formed of a biocompatible material such as PMMA. About the outer periphery of the ring housing element 152 are peripheral apertures 152A that are dimensionally adapted for receiving a strand of suture therethrough to thereby allow the suturing to be fixedly engaged against the tissue within the eye.

The adjustable imaging lens element 136 is dimensionally adaptive for fitting within a posterior nipple extending from the ring assembly 152. The illustrated lens element 136 is a plural lens assembly housed within an expandable housing element 136A. The housing element 136A can be axially expanded relative to the longitudinally extending axis 170 depicted in FIG. 2. As such the lens element 136 can be adapted to adjust the focal length of light traveling through the central apertures by the elements depicted in FIGS. 1 and 2.

The lens element 136 can be fluidicly sealed in the suture ring 152 by the sterile cover 154 that can fittingly engage about the nipple extending from housing ring element 152.

Figure 3:
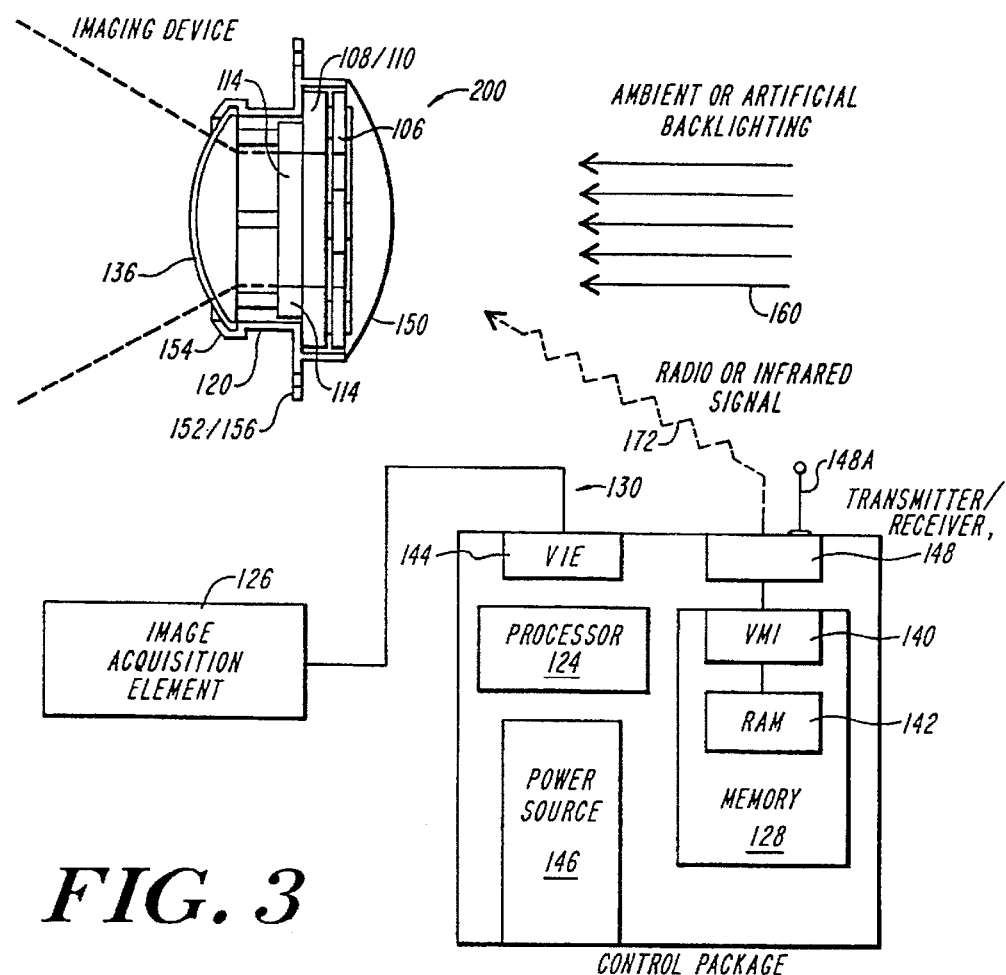

FIG. 3 illustrates the electronic keratoprosthesis system 200 and illustrates the image source element 130 that generates data signals which are transmitted to the receiver element 108 for controlling the display element 114 and thereby modulating the incident light 160 to generate images that are detectable by the retina. The image source element 130 illustrated in FIG. 3 includes a processor element 124, a memory 122, a video memory interface (VMI) 140, a random access memory element (RAM) 142, a video interface element (VIE) 144, a transmitter receiver element 148, with an optional antenna 148A, and power source 146. The illustrated image source control element 130 includes an optional image acquisition element 126 that connects via a transmission path to the video interface element 144.

As will be described in greater detail hereinafter the image source element 130 can generate data signals that can be transmitted via the transmitter element 148 to the receiver element 108 for modulating the ambient light 160 to generate images that are projected onto the retina.

Figure 4:
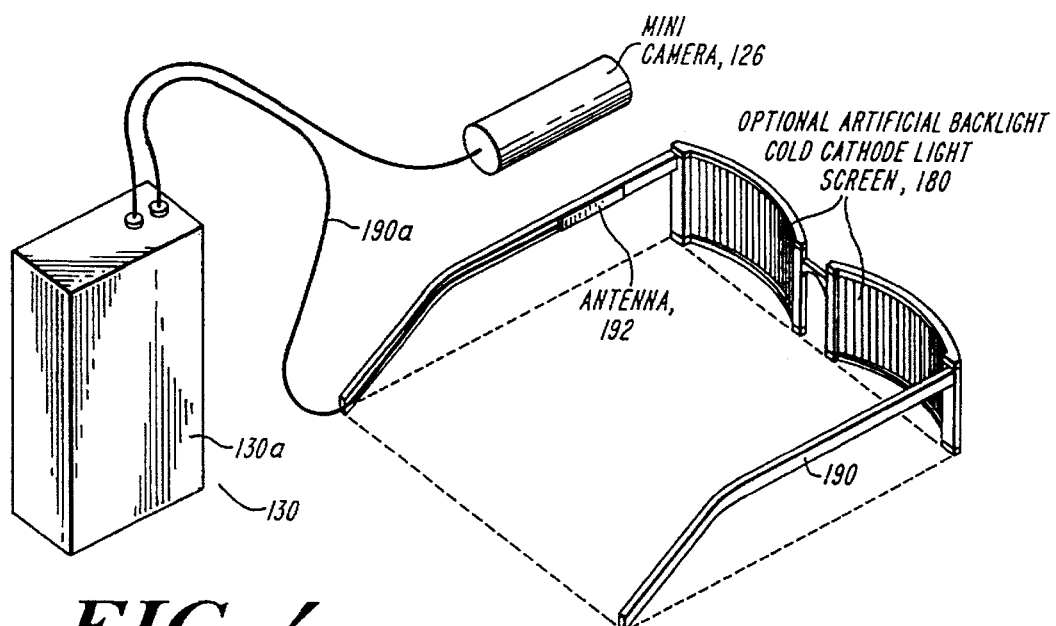

FIG. 4 illustrates an optional, yet preferred embodiment of the present invention that includes the image source element 130 in a housing 130A that is dimensionally adapted to be carried by the patient. In this embodiment the power source element 146 can be a battery pack of the type commonly used in portable electronic devices. The image acquisition element 126 illustrated in FIG. 4 is a mini-camera, of the type manufactured by the Sony Corporation, that generates video image signals that are transmitted to the image source element 130. FIG. 4 further illustrates that the element 130 connects via a transmission line 190A to an antenna element 192 that is mounted to a frame 190 that is constructed similar to a pair of eyeglasses. The antenna 192 illustrated in FIG. 4 is an antenna adapted for transmitting radio frequency electromagnetic signals to a receiver element 108 within the system 200. In the illustrated embodiment, the antenna element 192 is placed proximate to the electronic kerato prosthesis mounted within the patient's eye. As further illustrated the frames 190 have a light element 180 mounted in such a way as to provide a source of light 160. In a preferred practice of the present invention, these optional light elements 180 are cold cathode light screens of the type commonly used for providing a source of light.

Figure 5:
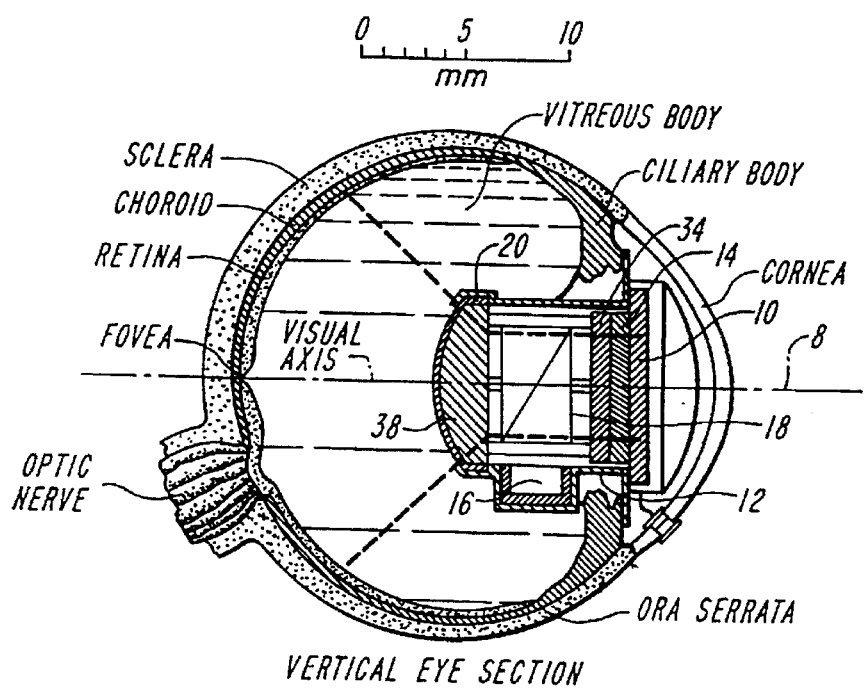
FIGS. 5–7 are system block diagrams of a second embodiment of an apparatus constructed according to the present invention for projecting an image signal onto a retina.
Figure 6:
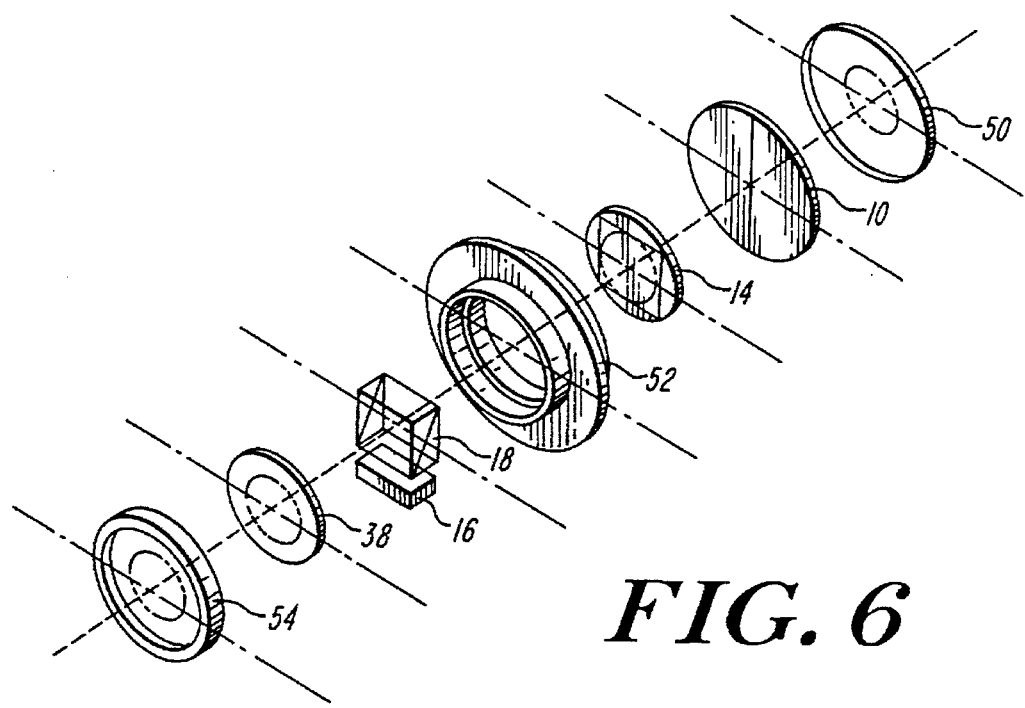
Figure 7:
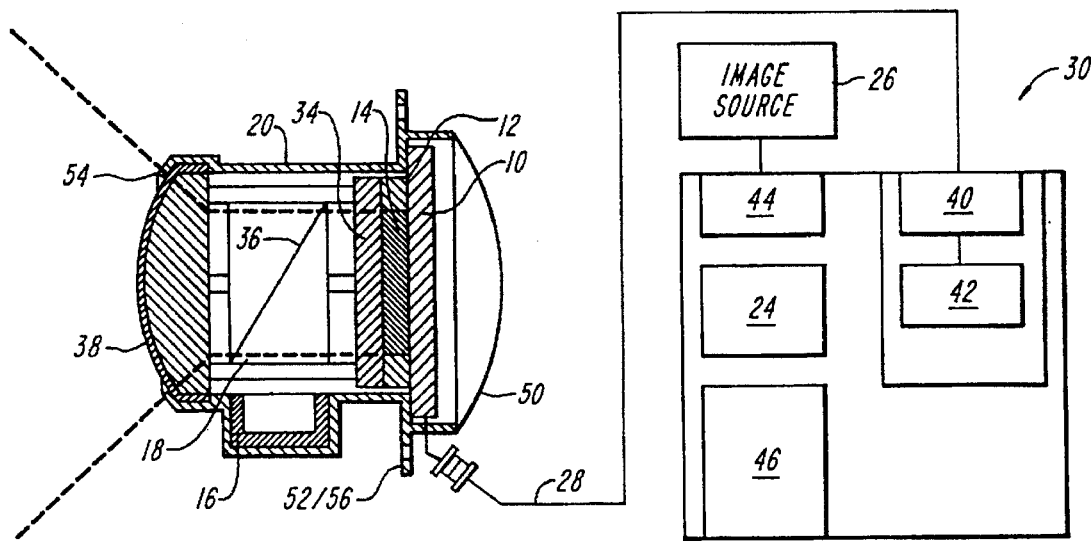

FIGS. 5, 6 and 7 illustrate an alternative embodiment of the present invention for projecting an image onto the retina of an eye. The illustrated keratoprosthetic system 8 includes a projection element 12 having a display device 14, a display driver element 10, an illuminator element 16, a beam splitter element 18 and a focusing element 20. As illustrated in FIG. 7, system 8 further includes an image memory element 22, a processor 24, an image acquisition element 26, a data power cable 28, video interface 40, memory element 42 and video interface 44.

The illustrated system 8 includes an intra-ocular kerato-prosthesis that couples via the cable element 28 to an image source 30. In the illustrated embodiment, the image source 30 includes the image memory element 22, the processor 24, the image acquisition element 26 and the cable element 28. The image source 30 can generate or acquire images for projection onto the retina. In the illustrated example, the image source 30 can use the optional image acquisition element 26, that can be a conventional video camera, to acquire video images as video signals. The acquired video signals can be transmitted to the processor 24 and stored in the image memory element 22. The processor 24 can display the stored image signals on the display device 14 of the projection element 12.

The illustrated projection element 12, that includes the display element 14 and display driver element 10 connected to the processor 24, can project the images generated by the display 14 onto the retina of the eye. The illustrated projection unit 12 projects the images displayed on the device 14 by providing an illumination element 16 and a beam splitter element 18. The illumination element 16, that can include a small mag-light can project light into the beam splitter element 18. The beam splitter element 18 can reflect a portion of the light onto the display 14. When the light from the illumination element 16 reflects on the display 14, the image on the display reflects back through the beam splitter 18 and to the focusing element 20.

The illustrated focusing element 20 optically couples with the projection element 12 and focuses the projected image from the display 14 onto the retina. The illustrated focusing element 20 includes an adjustable imaging lens 38 fitted within a nipple extending from the housing element 52. The focusing element 20 acts like the crystalline lens of a normal healthy eye, which focuses the images transmitted through the cornea onto the retina at the back of the eye. The focusing element 20 can be an adjustable telescoping element that includes plural lens elements disposed within an housing that is expandable along the axis of the optical path of the projected image. The expandable housing can include a locking mechanism to lock the housing to prevent movement once the device 8 is implanted. In operation, the operating surgeon can expand the housing to achieve the select focal length, then lock the housing before implanting the element in the eye.

In an optional embodiment, the focusing element 20 can further include a steering element, such as a mirror pivotably mounted within the housing and optically coupled with the projected image. The steering element can be selectively pivoted to direct the image to a select portion of the retina. This steering element provides a system that adjusts the focal position to accommodate blind spots that result from optical neuropathy and other conditions.

As can be seen from the above description, the system 8, that includes a image source 30, a projection element 12 and a focusing element 20, can project images onto the retina of an eye even if the eye has a substantially opaque or damaged cornea. In the illustrated embodiment, the projection unit 12 and the focusing elements 20 form an electronic intra-ocular prosthesis that can be surgically implanted into the eye behind the cornea. The image source 30 that includes the memory element 22 can be positioned exterior to the eye and connected to the projection unit 12 by the data cable 28. The image source 30, projection element 12 and focusing element 20 act in concert to generate and project images onto the retina of the eye without requiring an transparent optical couple at the anterior portion of the eye.

The illustrated projection unit 12 includes a display device 14 that is dimensionally adapted to fit within the eye at a position posterior to the damaged cornea. In one embodiment of the present invention, the display device 14 is a light valve type display such as a passive matrix liquid crystal display of the type having liquid crystals that can act as pixels that selectively transmit or block ambient lighting, back lighting, side lighting or other light source, to form an image. As can be seen in FIGS. 5 and 6, the display device 14 can be a flat panel display about the size of a contact lens, and can have dimensions of 7 mm diameter and 1 mm thick.

The illustrated passive display device 14 can include a dimensionally adapted conventional liquid crystal display that uses a liquid crystal, such as the type that contain the rod-like molecules cyanobiphenyls that respond to electrical fields by reorienting themselves along electrical field lines to transmit or to block a lighting source used to create the image. The passive liquid crystal display device 14 can be selected from the family of 90° twisted nematic field effect LCDs. With no voltage field applied to a given pixel, the rod-like molecules which are next to the electrodes on the glass substrate of the LCD panel device 14, are aligned at 0° relative to an axis extending along the surface of the panel. The pixels will gradually rotate through the liquid crystal film until they are at 90° next to the opposite substrate. Polarized light passing through the liquid crystal is rotated 90°, allowing the light to pass through a polarizing film on the other side of the illustrated passive LCD display device 14. When pixel voltage is applied, the liquid crystal molecule align themselves perpendicularly to the panel relative to the axis. No polarity rotation takes place and light is blocked by the polarizing film.

By selectively controlling which pixels in the display 14 block light and which pixels in the display 14 pass light, images are created on the display 14. One such display device 14 that can be employed with the present invention is the µ-display developed by The Massachusetts Institute of Technology.

In the illustrated embodiment, and as described above, the display device 14 is a passive matrix LCD display and therefore generates no light and requires a lighting source in order to generate perceptible images. The illustrated illuminator element 16, that is optically coupled to the display device 14, generates the light for projecting the image formed by the pixels in display device 14 to the retina. In the illustrated embodiment of the present invention, the illuminator element 16 is a simple mag-light, or pen light, illumination element that generates visible light. The visible light generated by the mag light element is optically coupled to the display device 14 via the beam splitter 18.

In an alternative embodiment of the present invention, the display device 14 is an active matrix display. The active matrix display device 14 actively generates an image that can be focused onto the retina by the focusing element 20. In this embodiment, the illuminating element 16 is incorporated into the display device 14 in the form of the active photo transistors that generate light response to control signals generated by the image source 30.

With reference again to the embodiment of the FIGS. 5–7 that employs a passive matrix display panel, the illustrated beam splitter 18 reflects the visible light generated by the illuminator element 16 onto the display device 14. The visible light first passes through the optional polarizing filter 34 positioned posterior to the display element 14. The polarizing filter 34 can be a conventional polarizing filter of the type commonly used with passive matrix LCD displays such as the illustrated display 14 and can be part of the display device 14, or can be a separate polarizing filter positioned in front of the display device 14. The polarizing filter 34 can be a thin film polarizing filter of the type generally known in the art of optical engineering. The polarizing filter 34 is dimensionally adapted for being implanted into an eye as part of the electronic prosthesis. Preferably the polarizing filter 34 has a thickness of less than a millimeter and a height and width roughly equal to the diameter of a conventional contact lens. The construction of such a polarizing filter 34 is considered well known in the art of optical engineering and any additions, substractions or modifications to the polarizing filter 34, or the inclusion of a plurality of polarizing filters 34, does not depart from the scope of the present invention that provides an electronic keratoprosthesis for implanting into an eye.

The illuminator element 16 can include a mag-light that is a low power visible light source, such as a conventional mag-light unit. However, it should be apparent to one of ordinary skill in the art that other mag-light elements that can generate light suitable for reflecting the image generated by the display panel 14, can be practiced with the present invention without departing from the scope thereof.

The device 8 illustrated in FIGS. 4 and 5 includes a beam splitter element 18 that optically couples the illuminator element 16 to the passive display device 14. The beam splitter 18 in the illustrated embodiment includes a halfway transmissive mirror 36 that is angularly oriented within the beam splitter 18 to reflect light from the illuminator element 16 at a 90° angle onto the display device 14. Light reflected from the display panel 14 passes through the transmissive mirror 36 and passes into the focusing element 20. The beam splitter 18 is dimensionally adapted for implanting into an eye and can be approximately 6 mm wide, 6 mm in length and 4 mm in thickness.

In one embodiment of the prosthesis, 8 the beam splitter 18 is a cube beam splitter of the type manufactured by Melles Griot Company of Irvine, Calif. It should be apparent to one of ordinary skill in the art that any optical coupling elements that can couple the illumination element 16 with the display device 14 can be practiced with the present invention without departing from the scope thereof. Furthermore, it should be apparent to one of ordinary skill in the art of optical engineering that the beam splitter element 18 of the illustrated prosthesis 8 is part of the illumination system that provides light to the display device 14. Therefore, in other embodiments of the present invention, the illumination element 16 can be repositioned within the prosthesis and alternative configurations can provide light to the passive display 14 either as back-lighting, side-lighting, or other lighting configuration.

The focusing element 20 depicted in FIG. 5 is optically coupled by the beam splitter element 18 to the display device 14. The focusing element 20 can include one or more lenses 38 that focus the reflected image generated by the display device 14 onto the retina of the eye. The construction of such an adjustable lens is within the scope of one of ordinary skill in the art of optical engineering.

The illustrated image source 30 connects via the data cable element 28 to the projection element 12. The image element 22 stores image signals that the processor 24 can use to control the pixels of the display device 14 to generate images on the display device 14. The stored image signals can represent alphanumeric characters, icons, video images, graphic images, or any other type of image that can be displayed with the display device 14. Therefore, the image memory element 22 is constructed as a video buffer memory that stores the images which will be projected onto the retina of the eye and perceived by the patient.

The image memory element 22 can be an electrical circuit card assembly that includes a random access memory. The processor 24 can write image signals into the image memory element 22. The image memory element 22 can contain a flat panel display device video memory interface 40 that connects to the data cable element 28. The video memory interface 40 can configure the pixels of display element 14 according to the video signals stored in the random access memory 42. In one embodiment of the invention the video memory interface 40 can be compatible with a simple matrix or passive matrix flat panel display and can apply pixel data as voltage signals row by row to the display 14. The row of pixels can be lighted by applying a common voltage to a row electrode stripe on the display 14, while applying the appropriate voltages to each pixel on a column electrode stripe of the display 14 to achieve the desired brightness of each pixel in the row. Therefore, the video interface 40 can activate each pixel once per picture frame, and a picture frame can be represented by a single image signal stored in the random access memory 42.

In a preferred embodiment of the invention, the image memory element 22 can store video image signals. In this preferred embodiment the random access memory 42 can be configured as a video buffer that stores one or more image signals where each image signal is representative of a single picture frame. The video memory interface 40 can read each image signal sequentially from the memory 42 for displaying the image signals sequentially on the display device 14. Each image signal is displayed at the selective frame rate of the image source 30, such as at a frame rate of 30 frames per second. Alternatively, the video memory interface 40 can be an active matrix video interface for controlling an active matrix display device 14. The active matrix video interface can include an electronic switching assembly that has an electronic switching device for each pixel in the active matrix display device 14. The video interface can illuminate each pixel in the display 14 by applying a voltage to each thin filmed transistor in the active matrix display 14.

In a further alternative embodiment, the video memory interface 40 can be a simple segment display interface that activates segments of the display 14 to generate image signals that represent characters such as text or numbers. In this embodiment of the invention, the random access memory 42 can store electrical data signals representative of text, numbers, or other symbols known to the interface 40 and the interface 40 can activate the appropriate pixels or segments in the display device 14 to generate images of the characters represented by the image signals stored in memory 42.

In the system depicted in FIG. 7, the image memory element 22, that includes the random access memory 42 and the video interface circuit 40, connects via a data cable 28 to the display device 14. In an alternative embodiment of the present invention, the image memory element 22 can be incorporated into an integrated circuit disposed on the display device 14. These and other configurations of the illustrated prosthetic system 8 can be practiced with the present invention without departing from the scope thereof.

FIG. 7 depicts a processor element 24 that can generate image signals and store the image signals in the image memory element 22. The processor element 24 can be an electrical circuit card assembly of the type commonly used for generating digital data signals representative of image signals. In one embodiment of the present invention, the processor 24 can be a conventional computer system such as a personal computer or a workstation. The processor 24 can include a processing unit, program memory, and data memory. The processing unit 24 can operate according to a set of program instructions stored in the program memory. The program instructions can operate the processing unit 24 to generate image signals and for storing the generated image signals in the memory element 22. In one embodiment of the present invention, the processor 24 generates image signals representative of alpha numeric characters, such as the text of a book, and stores these generated image signals in the memory element 22 for display by the display device 14.

Optionally, the processor 24 can include a video interface 44 that connects to an image collection element, such as the image acquisition element 26, and to the processor 24. The video interface 44 can collect video image signals that the processor 24 can store as image signals in the memory element 22. As depicted in FIG. 7, the video interface 44 connects to the image collection element 26 such as a digital electronic camera. The image collection element 26 can generate image video signals for display by the display device 14. In one embodiment of the invention, the image collection element 26 is a conventional video camera such as the type that produces video image signals compatible with the RS-170 standard. The processor 24 can transform the RS-170 video signals into a format suitable for storage in the memory element 22, and the video memory interface 40 can control the display device 14 to generate images representative of the images captured by the collection unit 26. In this way, the prosthetic system 8 depicted in FIG. 7 can project image signals onto the retina of an eye having an opaque cornea and provide the patient with the visual images collected by the camera 26. In a preferred embodiment of the invention, the collection element 26 is a video camera of the type manufactured by the Sony Corporation. Preferably the video camera is a miniature pen size video camera that can be carried by the patient on a pair of eyeglass frames.

The image source 30 also includes a power supply 46. In one embodiment of the invention the power supply 46 is a small battery pack and switching supply that generates the voltage supply signals necessary for driving the processor 24, the collection element 26, the projection unit 12 and the illuminator element 16. In an alternative embodiment of the present invention, the power supply 46 is the power supply of the processor 24 that can be a conventional personal computer or work station.

The data power cable element 28 can connect between the image source 30 and the display device 14. The data power cable element 28 can enter the eye through a cervical canal which perforates the exterior of the eye. The exterior sheath of the cable 28 that contacts biological tissue can be made from a biocompatible material such as PMMA.

FIGS. 8, 9, 10 and 11 illustrate an alternative embodiment of the present invention for projecting an image onto the retina of an eye. The system 68 depicted in FIG. 8 includes an image source 86 with an optional image acquisition element 86A. The illustrated image acquisition element 86A can be a video camera of the type commonly employed to generate video image signals representative of a visual image. The illustrated projection element 70 is in electrical circuit with the image source element 86 and receives signals suitable for modulation by the projection source 70. The source 70 mounts to a frame 70A that is worn by the patient similar to a pair of eye glasses. The frames 70A include mirrored surfaces that reflect the projected image back toward the eye of the patient, and projects the image against the corneal tissue thereon.

Figure 8:
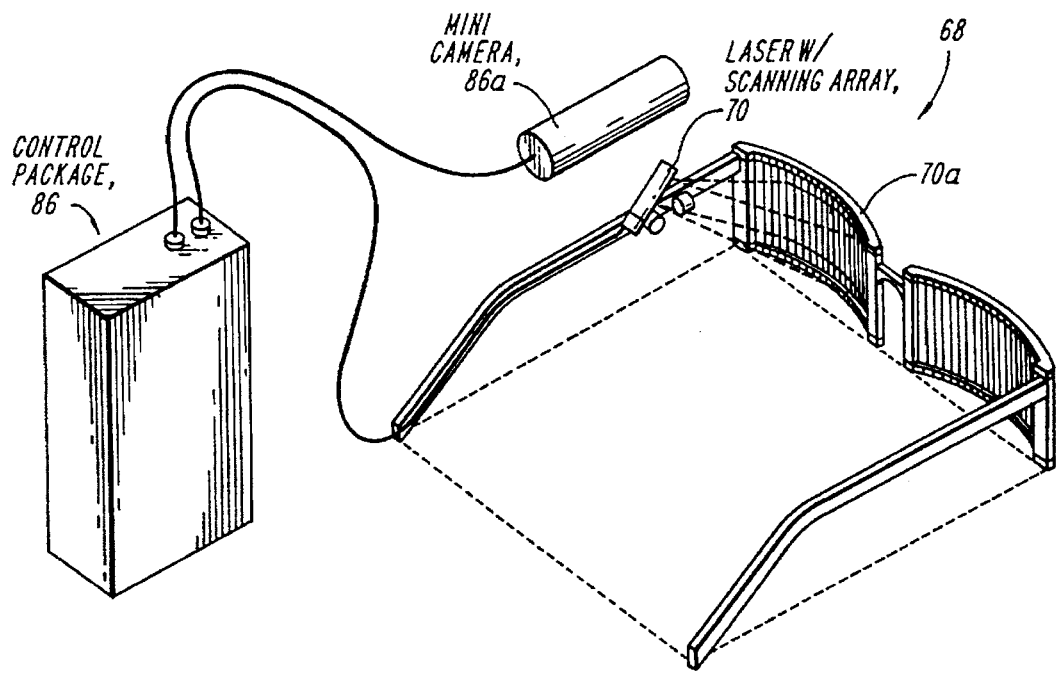
FIGS. 8, 9, 10 and 11 are system block diagrams of an alternative embodiment of an apparatus for projecting an image signal onto a retina.
Figure 9:
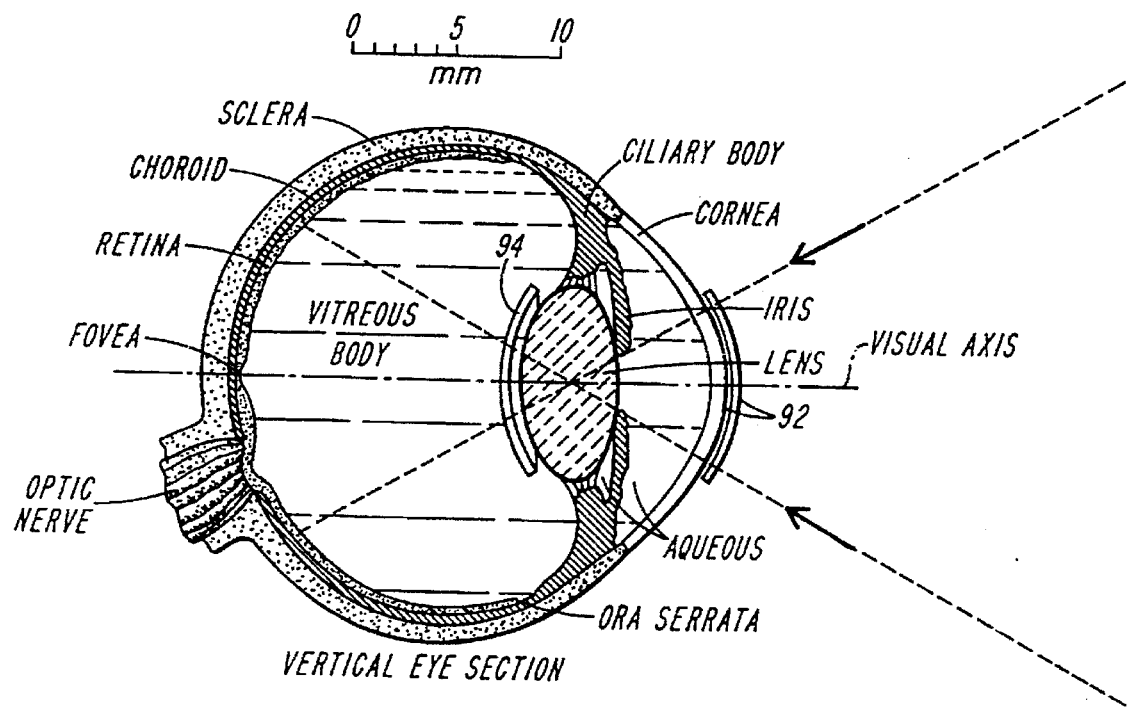
Figure 10:
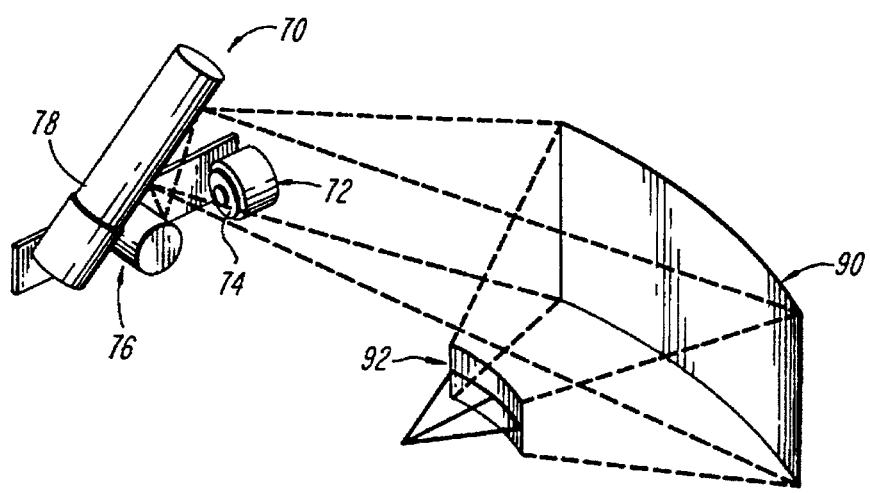
Figure 11:
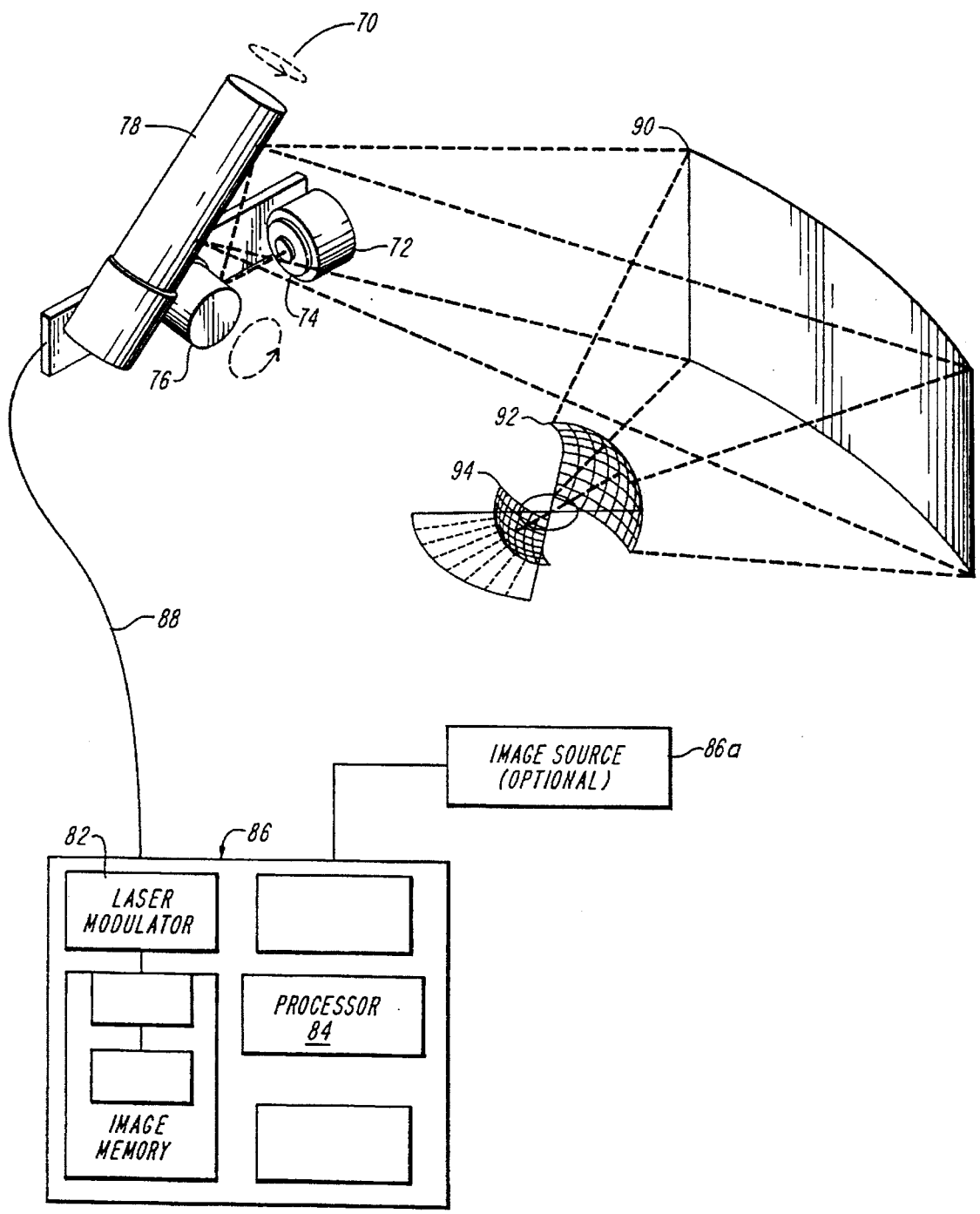

FIGS. 9, 10 and 11 illustrate in more detail the system 68 depicted in FIG. 8. The system 68 includes a projection element 70 that includes a laser diode 72, a high speed shutter element 74, a horizontal scanning mirror element 76 and vertical scanning mirror element 78. This system further includes a focusing element 94, an image memory element 80 and a data processing element 84.

With reference to FIG. 11, the illustrated system 68 includes an image source generator 86 that has the processing element 84, the image memory element 80 and a laser modulator element 82. The image source generator 86 connects to the laser diode 72 via a transmission path 88. The laser diode 72 generates a beam of coherent energy that can be modulated by a high speed shutter element 74 and scanned across the surface of the opaque cornea by the scanning mirrors 76 and 78.

The system 68 depicted in FIGS. 8, 9, 10 and 11 projects an image onto the retina of an eye by modulating the laser energy generated by the laser element 72 and by scanning the modulated laser beam across the opaque surface of the cornea. The modulated laser beam has sufficient intensity to pass through the substantially opaque cornea of the eye and to pass through the crystalline lens and the focusing element 94 to project an image against the retina of the eye. In one practice, the laser energy is modulated by selectively controlling the intensity of the light generated by the laser element 72. For example, the laser light can be modulated by selectively activating and deactivating the laser element 72. Alternatively, the laser light can be modulated by selectively increasing and decreasing the intensity of the laser light generated by the laser element 72. In the illustrated embodiment of FIGS. 8–11, the laser light is modulated by a high speed shutter 74 and is coordinated with the scanning mirrors 76 and 78 so that the modulated signal generates a recognizable image pattern when projected against the opaque cornea and passed through to the retina.

In the depicted embodiment, the scanning mirrors 76 and 78 are polygonal scanning mirrors that couple to motor assemblies (not shown) which rotate the polygonal mirrors about a selected axis in order to scan the laser light across a select portion of the cornea. Preferably the polygonal mirrors 76 and 78 are dimensioned for scanning a collimated narrow laser beam of approximately 1 mm in diameter.

In another embodiment of the invention, the laser beam can be scanned in the vertical and horizontal directions by two acousto optic crystals.

The laser element 72 can be a laser diode of the type commonly used for producing a narrow coherent beam of radiant energy. In one embodiment of the present invention the laser element 72 includes a laser diode manufactured by the Melles Griot Company of Irvine, Calif.

A focusing element 94 illustrated in FIG. 9 can be an intra-ocular lens positioned posterior to the cornea. The focusing element 94 can be formed from a biocompatible material, and preferably is formed from a material such as PMMA.

The image source 86 can generate control signals for the laser element 72 that modulate image signals stored in the image memory element 80 to project the stored image signals as images onto the opaque cornea 92. The image source generator 86 can include a processing element 84 that can be a conventional personal computer of workstation. The image memory element 80 can be a conventional computer memory that includes a random access memory for addressably storing image signals. The image memory element 80 can connect to via a transmission path to the laser modulator element 82. The laser modulator element 82 can be a conventional circuit for modulating the intensity of a laser element.

In another aspect of the invention, methods are provided for projecting an image onto a retina. In one practice, the method can include the steps of providing an image memory element that is suitable for storing one or more image signals representative of a visual image, providing a projection element as described above, that couples in circuit with the image memory element and the further step of implanting a focus element into the vitreous cavity of an eye, and surgically attaching the focus element within the vitreous cavity. Once the system is implanted and attached, images are provided to the image memory element for transfer to the projection element that projects the images onto the retina, via the focus element that focuses the projected images.

In one practice of the invention, a display panel device and focus element are implanted into the eye and attached therein. The patent wears a pair of eye glass frames that include a light source that projects light toward the eye, at a sufficient intensity to penetrate the cornea. The light travels through the display panel, while images are displayed thereon, and the generated modulated optical images signal are projected through the focus element and onto the retina.

Other practices of the invention have been described and are also readily discernible by one of ordinary skill within the art of ophthalmology from the preceding description of the illustrated embodiments.

The invention has been described above with reference to certain illustrated embodiments. The description of the illustrated embodiments provided more fuller understanding of the invention, however, the invention is not to be limited to the illustrated embodiments, or the description thereof, and the invention is to be interpreted according to the claims set forth herein.

We claim:

1. Apparatus for projecting an image onto the retina of an eye having a substantially impaired cornea, comprising means for generating an image signal representative of a visual image, an image memory element for storing said image signal, projection means, coupled with said image memory element, for generating an optical image signal in response to said image signal, for detection by a retina, and being representative of the visual image, and focus means for being implanted within an eye at a position anterior to the retina and being optically coupled to said projection means for focusing said optical image signal onto the retina.

2. Apparatus according to claim 1 wherein said projection means comprises a display device dimensioned for disposition within the eye.

3. Apparatus according to claim 2 wherein said image memory element includes a data cable and is in circuit with said projection means via the data cable.

4. Apparatus according to claim 1 wherein said projection means comprises a liquid crystal display device dimensioned for disposition within the eye at a position posterior to the cornea and having an illuminator element optically coupled to said display device.

5. Apparatus according to claim 4 wherein said projection means comprises a beam splitter means for optically coupling said illuminator element to said display device and for optically coupling said display device to said focus means.

6. Apparatus according to claim 1 wherein said projection means comprises a laser diode element and a scanning mirror that is optically coupled to the laser diode.

7. Apparatus according to claim 6 wherein said scanning mirror includes a polygonal scanning mirror and a motor element coupled to the polygonal scanning mirror for rotating the polygonal mirror relative to an axis extending through said polygonal mirror.

8. Apparatus according to claim 1 wherein said projection means comprises a horizontal scanning mirror element for scanning a beam of radiation horizontally across the retina and a vertical scanning mirror element for scanning the beam of radiation vertically across a retina.

9. Apparatus according to claim 1 wherein said projection means comprises an acoustic-optic crystal element for scanning a beam of radiation across the retina.

10. Apparatus according to claim 1, wherein said means for generating an image signal comprises an image collection means, in circuit with said image memory element.

11. Apparatus according to claim 10 wherein said image collection means comprises a digital camera element having a charge coupled device.

12. Apparatus according to claim 10 wherein said image collection means comprises a data processor element having an image signal generator for generating electrical data signals representative of visual images.

13. Apparatus according to claim 1 wherein said memory element comprises an electrical circuit data memory suitable for storing electrical digital data signals representative of visual images.

14. Apparatus according to claim 1 wherein said focus means comprises a lens element having a focal length adapted for projecting said optical image signal onto a select portion of the retina.

15. Apparatus according to claim 14 wherein said lens element comprises a biocompatible material.

16. Apparatus according to claim 14 wherein said lens element comprises polymethyl-methacrylate.

17. Apparatus according to claim 14 wherein said lens element includes an expandable housing and plural lens elements disposed within said expandable housing.

18. Apparatus according to claim 14 wherein said lens element includes a steering element for directing said optical image signal to a select portion of the retina.

19. Apparatus according to claim 1 further including a housing element having engagement means for fixedly engaging to the tissue within the eye.

20. Apparatus for projecting an image onto a retina of an eye, comprising means for generating a data signal, a projection element having a display device dimensioned for implantation into the eye, and a display driver element arranged in circuit with said display device and having means for receiving said data signal and for operating said display device to generate an optically detectable image responsive to said data signal, and a focus element optically coupled with said display device and adapted for focusing said optically detectable image onto the retina of the eye.

21. Apparatus according to claim 20 wherein said display device is a passive display panel element and said focus element, display panel element and said driver element are arranged to define an optical path that extend through each said element.

22. Apparatus according to claim 21 further including an eye glass frame and a light source disposed on said eye glass frame to project light toward the eye.

23. A method for projecting an image onto the retina of an eye having a substantially impaired cornea, comprising the steps of generating an image signal representative of a visual image, storing in a memory element said image signal, generating an optical image signal in response to said image signal, said optical image signal being representative of the visual image, providing a focus element for implantation into the eye at a position anterior to the retina, implanting said focus element within the eye, and projecting said optical image signal to said focus element for focusing said optical image signal onto the retina.

\* \* \* \* \*